(12) United States Patent
Kim et al.

(10) Patent No.: US 9,186,135 B2
(45) Date of Patent: Nov. 17, 2015

(54) MEDICAL SUTURE HAVING MICRO COGS ON SURFACE AND METHOD OF MANUFACTURING THE SAME

(75) Inventors: Tae Jun Kim, Daejeon (KR); Byung Gwan Kim, Daejeon (KR); Daesung Song, Daejeon (KR)

(73) Assignee: HANSBIOMED CORP., Seoul (KR)

( * ) Notice: Subject to any disclaimer, the term of this patent is extended or adjusted under 35 U.S.C. 154(b) by 672 days.

(21) Appl. No.: 13/580,627

(22) PCT Filed: Aug. 29, 2011

(86) PCT No.: PCT/KR2011/006361
§ 371 (c)(1),
(2), (4) Date: Aug. 29, 2012

(87) PCT Pub. No.: WO2012/128432
PCT Pub. Date: Sep. 27, 2012

(65) Prior Publication Data
US 2013/0072971 A1    Mar. 21, 2013

(30) Foreign Application Priority Data
Mar. 24, 2011  (KR) .................. 10-2011-0026122

(51) Int. Cl.
*A61B 17/04* (2006.01)
*A61B 17/06* (2006.01)
*A61L 17/14* (2006.01)
*D02J 3/00* (2006.01)
*A61B 17/00* (2006.01)

(52) U.S. Cl.
CPC ........... *A61B 17/06166* (2013.01); *A61L 17/14* (2013.01); *D02J 3/00* (2013.01); *A61B 2017/00526* (2013.01); *A61B 2017/00831* (2013.01); *A61B 2017/06176* (2013.01)

(58) Field of Classification Search
CPC .................................................. A61B 17/06166
USPC .................................. 606/228, 229, 230, 231
See application file for complete search history.

(56) References Cited

U.S. PATENT DOCUMENTS

| | | | |
|---|---|---|---|
| 8,454,653 B2 * | 6/2013 | Hadba et al. ................... | 606/228 |
| 8,663,277 B2 * | 3/2014 | Collier et al. .................. | 606/228 |
| 8,936,619 B2 * | 1/2015 | Odermatt et al. .............. | 606/228 |
| 2008/0161850 A1 | 7/2008 | Weisenburgh et al. | |
| 2010/0211098 A1 | 8/2010 | Hadba et al. | |
| 2011/0125188 A1 * | 5/2011 | Goraltchouk et al. ......... | 606/228 |
| 2011/0282386 A1 * | 11/2011 | Friedrich et al. .............. | 606/228 |
| 2012/0136388 A1 | 5/2012 | Odermatt et al. | |

FOREIGN PATENT DOCUMENTS

| | | |
|---|---|---|
| CN | 1830200 A | 9/2006 |
| CN | 1950034 A | 4/2007 |
| CN | 101027168 A | 8/2007 |

(Continued)

*Primary Examiner* — Vy Bui
(74) *Attorney, Agent, or Firm* — Birch, Stewart, Kolasch & Birch, LLP

(57) ABSTRACT

Provided are a medical suture having micro cogs on a surface thereof and a method of manufacturing the medical suture. The method of manufacturing a medical suture includes steps of: producing a suture preform where micro cogs are formed on a surface thereof by heating and pressing a raw material of a suture for surgery in an overflow mould in a heat-press solid-phase forming method; and producing a suture with twist maintained by applying a tensile force and a rotational force to the suture preform in a vacuum state where a specific temperature condition is maintained.

14 Claims, 2 Drawing Sheets

(a)

(b)

(56) References Cited

FOREIGN PATENT DOCUMENTS

| DE | 10 2008 057 216 A1 | 5/2010 |
| WO | WO 2009/129251 A2 | 10/2000 |
| WO | WO 2006/099703 A2 | 9/2006 |

* cited by examiner (a)

(b)

(a)

(b)

(c)

(a)

(b)

MEDICAL SUTURE HAVING MICRO COGS ON SURFACE AND METHOD OF MANUFACTURING THE SAME

BACKGROUND OF THE INVENTION

1. Field of the Invention

The present invention relates to a medical suture having micro cogs on a surface thereof and a method of manufacturing the medical suture.

2. Description of the Related Art

From the second half of the 1960s, in order to finish suturing tissue without knotting the suture, a barbed suture having barbs which are formed by cutting an outer portion of the suture has been tried to be used for suturing tissue. In the barbed suture, one or more micro cogs are formed on a surface of the suture at a predetermined interval. If the suture is inserted in one direction and tension is applied to pull the suture in the opposite direction, the barbs formed on the surface of the suture are firmly engaged with the tissue. Therefore, unlike a general suture, the barbed suture is used without knotting.

In the 1990s, Ruff in North Carolina of US and Sulamanidze in Russia published a new form of a medical barbed suture which could be used for surgical suturing, facelift for removing wrinkles in a face, a neck, a chest, and the like or pulling face tissue, and plastic surgery for removing wrinkles. In addition to the barbed suture, various medical sutures for anchoring tissue have been used for two purposes, that is, knot-free suturing and facelift.

As a representative method of manufacturing a barbed suture for surgical tissue suturing and plastic surgery, cutting methods are disclosed in US Patent No. 2004/0060410 titled by "Barbed Suture" and US Patent No. 2003/0041426 titled by "Method of Forming Barbs on a Suture and Apparatus for Performing Same". The cutting method is currently widely used, and most of suture products are manufactured according to the cutting method. However, the cutting method has the shortcomings as follows. Since the barbs are formed by cutting the surface of a spun thread of the suture, there is a limitation in size and thickness of the barb; since a distal end of the barb is too sharp, stimulus may be exerted on tissues or nerves in the vicinity thereof; since the spun thread of the suture is damaged due to the cutting, the strength thereof is greatly decreased in comparison with the suture having the same size; and since bio-absorption of relatively slender barbs formed by the cutting method is speedily made, a tissue anchoring ability is easily lost.

In order to compensate for the structural shortcomings in the barb formation, U.S. Pat. No. 7,582,105 discloses "Suture for Wound Closure, Tissue Approximation, Tissue Support, Suspension and/or Anchoration". In the invention, barbs are not formed in the suture, but knotting of the suture is performed with a predetermined interval, and a cone is suspended at each knot. However, in the invention, since the knots are formed in the suture, excessive folding and curving occur in the suture, and thus, the strength is greatly decreased at the knots, so that the function as a suture may be lost. In addition, the cone suspended to each knot is larger and harder than the barb. When the suture is inserted into a subcutaneous tissue, a patient may feel great pains due to damage to tissues and nerves.

Besides, US Patent No. 2006/005144 titled by "Tissue Holding Devices and Methods for Making the Same" discloses a pressing and die cutting method and an injection molding method as cited techniques. However, implementation of the invention is not assured, and the invention is not yet commercialized.

As described above, although various methods have been used for manufacturing a medical suture having a tissue anchoring function, the techniques for compensating for the shortcomings of the current products and capable of being immediately commercialized and practically used has been required to be developed.

SUMMARY OF THE INVENTION

The present invention is to provide a medical suture having micro cogs on a surface thereof which can be effectively used for surgical administration and a method of manufacturing the medical suture.

According to an aspect of the present invention, there is provided a method of manufacturing a medical suture including: (1) producing a suture preform where micro cogs are formed on a surface thereof by heating and pressing a raw material of a suture for surgery in an overflow mould at a temperature condition from a point less than a melting point of the raw material of the suture to a point more than a glass transition temperature at a pressure condition from 10 kgf/cm$^2$ to 200 kgf/cm$^2$ in a heat-press solid-phase forming method; and (2) producing a suture with twist maintained by heating the suture preform and applying a tensile force and a rotational force to the suture preform in a vacuum state where the temperature condition from a point less than the melting point of the raw material of the suture to a point more than the glass transition temperature is maintained.

According to another aspect of the present invention, there is provided a medical suture manufactured according to the aforementioned method, wherein cutting angles are not formed on the surface of the suture and the micro cogs are formed on the surface of the suture, wherein rotation per unit length of the suture is applied in a range from 72°/cm to 360°/cm, and wherein the micro cog has a directivity and has an anchoring ability by which the soft tissue is anchored in a direction opposite to an insertion direction when the suture is inserted to the soft tissue.

According to the present invention, it is possible to provide a medical suture having micro cogs on a surface thereof.

In the medical suture according to the present invention, a tensile strength thereof is in a level of from about 80% to about 90% of a tensile strength of a spun thread of the suture, and micro cogs having various shapes and size can be formed on an outer side of the suture.

According to the present invention, the micro cog has a directivity, so that the micro cog has an anchoring force for anchoring tissue in a direction opposite to an insertion direction when the suture is inserted into the tissue. Since the micro cog can be formed in various shapes and sizes, mechanical and biological tissue reactions occurring during the insertion into soft tissue can be designed in an optimization manner.

According to the present invention, it is possible to solve a problem of a tissue disintegration phenomenon in the related art in the case where a medical suture having bio-absorbable property for anchoring tissue is inserted into tissue. Namely, in this case, in the related art, since anchors (barbs, cogs, protrusions, conical hats) having a function of anchoring in a direction opposite to the insertion direction are absorbed into a body, the strength is greatly weakened and a tissue anchoring function is lost, so that the tissue disintegration phenomenon occurs. According to the present invention, since the size of the anchor (micro cog) can be adjusted, the time taken to completely dissolve the micro cog can be prolonged.

Therefore, the time when the tissue anchoring force is weakened can be delayed, and the initial anchoring force can be increased. Accordingly, it is possible to manufacture a medical suture having bio-absorbable property, anchoring tissue, and being appropriate for facelift.

DESCRIPTION OF THE PREFERRED EMBODIMENTS

Figure 1:
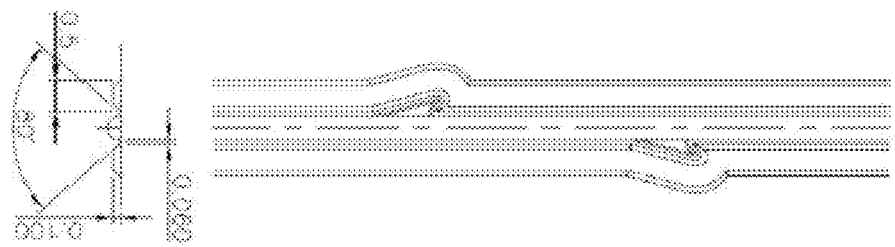
FIG. 1(a) is a view illustrating an overflow mould according an embodiment of the present invention.
FIG. 1(b) is a view illustrating an image thereof.
Figure 1:
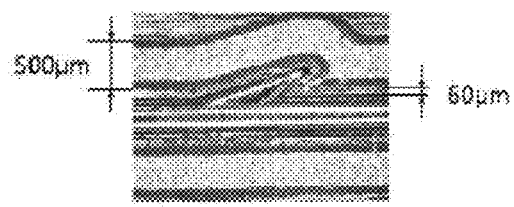

Hereinafter, a method of manufacturing a medical suture will be described in detail.

First, in a step (1), a raw material of a suture is heated and pressed under the condition of specific temperature and pressure by a solid-phase forming method, so that a suture preform having micro cogs on a surface thereof is produced.

The step (1) is based on molecular orientation and thermal properties of a raw material of a surgical suture made of medical polymers (hereinafter, referred to as a polymer suture). The polymer suture has directional molecular orientation in an inner portion thereof. Due to the directional molecular orientation, the polymer suture can maintain a high tensile strength. However, in the case where the polymer suture is heated in a range from a melting point to a point by 30° C. less than the melting point (Tm~Tm-30° C.), ductility of the polymer suture is increased or shrinking deformation occurs, so that the molecular orientation is lost. In addition, the tensile strength necessary for suturing tissue is lost.

However, although the polymer suture is in the heating range, in the case where the polymer suture is heated in the same range after the two ends are fastened so that the polymer suture is not shrunk and deformed, the ductility of the polymer suture is increased, and the tensile strength is maintained in the same level as that of the spun thread of the polymer suture.

The present invention utilizes the above properties of the polymer suture. The ductility is increased by heating the spun thread of the polymer suture up to a specific temperature less than the melting point of the raw material of the polymer suture; and the micro cogs are formed on the surface of the polymer suture by pressing the polymer suture in the state where the two ends thereof are fastened so as to suppress shrinking deformation. In this case, the micro cogs can be formed on the surface of the spun thread while the molecular orientation of the polymer suture is maintained.

According to the present invention, the raw material of the medical suture is a medical polymer having bio-absorbable property. More specifically, for example, polydioxanone, poly-(1-lactic) acid, poly-glycolic acid, and copolymers thereof can be selectively used. In the case of using the medical polymer having bio-absorbable property, the medical suture having bio-absorbable property can be manufactured.

In addition, the raw material of the medical suture may be a medical polymer having non-bio-absorbable property. More specifically, for example, polyprophylene, nylon, and mixtures thereof can be selectively used. In the case of using the medical polymer having non-bio-absorbable property, the medical suture having non-bio-absorbable property can be manufactured.

In the present invention, an overflow mould is used for manufacturing a suture preform. The overflow mould is configured to include a formation space and an overflow space. The formation space and the overflow space may be partitioned by a separation wall of which the thickness does not exceed 60 μm. Preferably, the gap between the formation space and the overflow space of the overflow mould is in a range from 30 μm to 60 μm. In the case where the gap between the formation space and the overflow space is large so as to exceed 60 μm, there is a problem in that, after the pressing formation, a product is not easily separated from a burr.

An introduction portion of the overflow space is configured to have an angle from 45° to 90°, more preferably, 80°. If the angle of the introduction portion of the overflow space is less than 45°, high pressure is needed for the pressing formation, and there is a tendency in that, after the formation, the product is not easily separated from the burr. If the angle of the introduction portion of the overflow space is more than 90°, there is a problem in that the formation portion of the mould is weakened.

The depth of the overflow space is controlled so that the depth of the overflow space is not larger than the depth of the formation space. Preferably, the depth of the overflow space is in a range from 50 μm to 100 μm. More preferably, the depth of the overflow space is set to 100 μm so that the product can be easily separated from the burr.

The width of the overflow space is formed along the boundary line with respect to the formation space. The width of the overflow space is in a range from 250 μm to 500 μm. More preferably, the width of the overflow space is 500 μm. If the width of the overflow space is large so as to exceed the above range, there is a problem in that the pressure applied to the overflow mould is increased, so that durability of the formation portion is weakened.

If the overflow space has a size in the ranges described above, after the heating and pressing formation of the medical suture, the burr occurring on the surface can be removed. If the overflow space has a size exceeding the ranges described above, the burr cannot be easily removed from the product, so that the medical suture cannot be manufactured.

FIG. 1(a) is a view illustrating an overflow mould according an embodiment of the present invention, and FIG. 1(b) is a view illustrating an image thereof. As illustrated in FIG. 1, if the formation space and the overflow space of the overflow mould are configured to satisfy conditions, a desired suture can be obtained.

The temperature used in the aforementioned step (1) is a specific temperature within a temperature range from a point less than the melting point of the raw material of the suture to a point more than a glass transition temperature. Preferably, the temperature is in a range from a point by 30° C. less than the melting point (Tm-30° C.) to a point by 15° C. less than the melting point (Tm-15° C.)

In the above step, in the case where the temperature is the room temperature, due to elasticity of the polymer suture, compression and expansion occur during the pressing formation. In other words, in the case where the polymer suture is pressed and formed at the room temperature by a strong force, when the compressing force is applied, the formation space is temporarily filled. When the compressing force is removed, some portion is expanded to be recovered, so that the burr portion between the moulds is shrunk. Therefore, the shape of the product becomes different from the shape of the formation space.

In the present invention, in order to overcome this problem, the temperature during the heating and pressing is adjusted to be within a temperature range from a point less than the melting point of the raw material of the suture to a point more than a glass transition temperature.

On the other hand, in the step (1), the pressure applied to the overflow mould is in a range from 10 kgf/cm² to 200 kgf/cm², more preferably, in a range from 80 kgf/cm² to 160 kgf/cm². In addition, the press can be appropriately used in a range from 15 ton to 50 ton. If the pressure is low (less than the lower limit of the above range), the burr is not removed from the overflow mould, there is a tendency in that the medical suture is difficult to manufacture. If the pressure is high (more than the upper limit of the above range), the durability of the mould is weakened, so that the formation portion may be deformed.

The suture preform is produced as a primarily-formed product by performing heating and pressing formation in the state where all the above conditions are satisfied. While the strength of the polymer suture is maintained in a level of from 80% to 90%, micro cogs are formed on the surface of the suture preform, and the burrs in the vicinity of the suture preform can be easily removed, so that the medical suture is appropriately manufactured.

Figure 2:
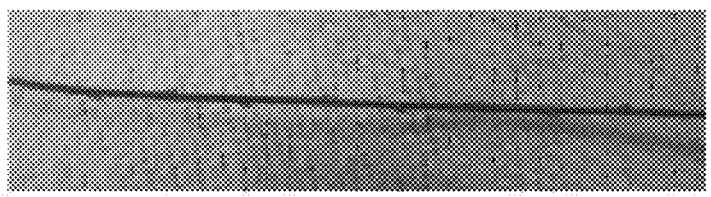
FIGS. 2(a) and 2(b) are views illustrating images of a suture preform as a primarily-formed product produced by a heating pressing formation method according to the present invention.
FIG. 2(c) is a view illustrating an image of deformation of a polymer suture during a pressing formation process.
Figure 2:
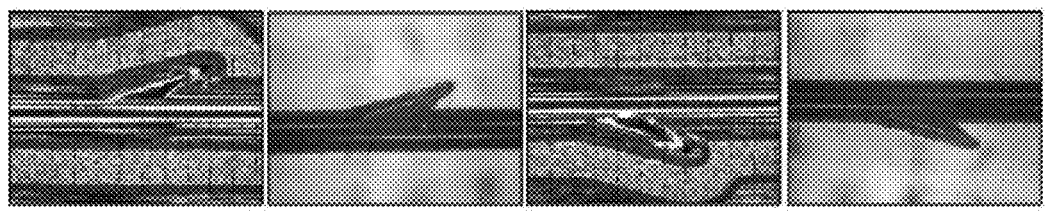
Figure 2:
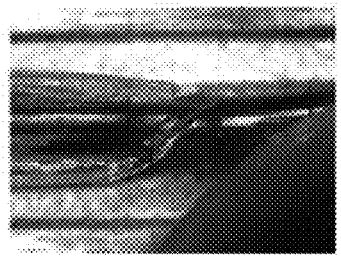

FIG. 2(a) is a view illustrating an image of an example of a suture preform; FIG. 2(b) is a view illustrating images of front surfaces and cross-sections of the suture preform; and FIG. 2(c) is a view illustrating an image of deformation of the polymer suture during the heating and pressing formation.

Next, in a step (2), a tensile force and a rotational force are applied to the suture preform in a vacuum state where the temperature condition from a point less than the melting point of the raw material of the suture to a point more than the glass transition temperature is maintained, so that the suture with twist maintained is produced.

In the step (2), the tensile force is applied to the suture preform, which is produced by performing heating and pressing in the step (1), in the state where the two ends are anchored, and terminal treatment is performed for a predetermined time, so that a suture is manufactured as a secondarily-formed product. At this time, the magnitude of the tensile force is a level of from 10% to 30% of the maximum tensile strength of the suture preform, more preferably, 20% thereof. The heating time is in a range from 24 hours to 48 hours in the vacuum state.

In addition, in the step, when the tensile force is applied, the rotational force is simultaneously applied, so that the twist occurs in the medical suture. Therefore, the micro cogs are positioned along the helical multi-directions. The magnitude of the rotational force is proportional to the length of the primarily-formed product, and the rotation angle of the two ends are in a range from 72°/cm (minimum) to 360°/cm (maximum). The temperature during the heating applied in the step is in a range from a glass transition temperature (Tg) to a melting point (Tm) of the raw material of the suture used for producing the suture preform, more preferably, in a range from a point by 30° C. less than the melting point (Tm-30° C.) to a point by 15° C. less than the melting point (Tm-15° C.)

In the medical suture manufactured according to the present invention, aciculae having a directivity are formed as an ideal shape of a cog. Since the cogs are formed by heating and pressing the spun thread of the suture, the cogs are positioned in a zigzag manner. Although the size of the micro cog positioned on the surface of the medical suture is determined in proportion to the size of the spun thread of the suture, it is preferable that the size of the micro cog is not larger than the diameter of the spun thread of the suture in terms of the formability of the product.

Figure 4:
FIG. 4(a) is a view illustrating an image of a barbed suture produced by a cutting method.
FIG. 4(b) is a view illustrating an image of a medical suture having micro cogs on a surface thereof produced according to the present invention.
Figure 4:
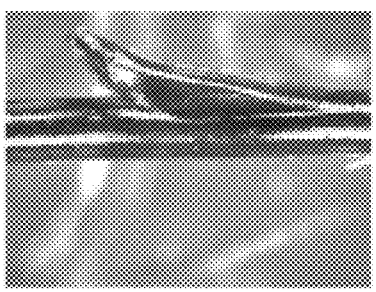

The medical suture manufactured according to the present invention has sufficient tissue anchoring ability necessary for surgical administration and has a function of facilitating regeneration of peripheral soft tissue. In addition, as illustrated in FIG. 4(a), the medical suture manufactured according to the present invention has no physical knot since a cutting angle is not formed by cutting the surface of the spun tread of the suture. Therefore, in the medical suture according to the present invention, while the strength of the suture having the same size is maintained to be in a level of from 80% to 90%, the micro cogs can be formed on the surface as illustrated in FIG. 4(b).

The medical suture according to the present invention is a medical suture where micro cogs are formed on a surface thereof by a method distinguished from the existing methods for a barbed suture or a tissue-anchoring suture. The medical suture is a medical suture which can be effectively used for suturing cut portions during a surgical operation and for facelift such as surgical lifting or sling administration for wrinkles in a face, a neck, a chest, and the like.

Hereinafter, the present invention will be described in detail with reference to embodiments. However, the present invention is not limited to the embodiment.

COMPARATIVE EXAMPLE 1

A polydioxanone suture made of a single fiber and having a USP1 size (diameter: 0.53 mm) was mounted and fastened to a general mould. Next, the suture was pressed and formed at a room temperature at a pressure of 7 kgf/cm² for 4 minutes. The thickness of a burr was 0.2 mm or more, and overflow space was not formed, so that a product was not separated from the burr. Therefore, a primarily-formed product was not formed.

COMPARATIVE EXAMPLE 2

A polydioxanone suture made of a single fiber and having a USP1 size (diameter: 0.53 mm) was mounted and fastened to a general mould. Next, the suture was pressed and formed at a temperature of 125° C. at a pressure of 7 kgf/cm² for 4 minutes. A product was securely separated from a burr, so that the burr was easily removed. Although the product was formed according to the formation space, due to the heating at the melting point or more, thermal decomposition occurred and the molecular orientation was lost. Therefore, the tensile strength was decreased down to the level of 40%. Accordingly, the product was not appropriate for a primarily-formed product.

COMPARATIVE EXAMPLE 3

A polydioxanone suture made of a single fiber and having a USP2 size (diameter: 0.59 mm) was mounted to an overflow mould. Next, the suture was pressed and formed at a room temperature at a pressure of 140 kgf/cm² for 5 seconds. The thickness of a burr was 50 µm or less. A product was securely separated from the burr due to the overflow space, so that the burr could be removed. However, the suture was fissured at the cross section of the suture due to a compression and expansion phenomenon. Therefore, the product was not appropriate for a primarily-formed product.

First Embodiment

A polydioxanone suture made of a single fiber and having a USP2 size (diameter: 0.59 mm) was mounted to an overflow mould. Next, the suture was pressed and formed at a temperature of 90° C. at a pressure of 140 kgf/cm² for 5 seconds. The thickness of a burr was 50 μm or less. A product was completely separated from the burr due to the overflow space without fissure. A primarily-formed product was heated in a vacuum state at a temperature of 90° C. for 24 hours in the state where a tensile force of 14N was applied to two ends thereof, so that the primarily-formed product was transformed into a secondarily-formed product. With respect to the size of a micro cog formed on the primarily-formed product, the height thereof was in a range from 380 μm to 400 μm, the length thereof was in a range from 1000 μm to 1100 μm, the front angle thereof was in a range from 160° to 165°, and the rear angle thereof was in a range from 38° to 40°. The compression and expansion phenomenon did not occur before and after the formation, and the formed product was formed according to the formation space. Therefore, the formed product was appropriate for the object of the present invention.

Second Embodiment

A polydioxanone suture made of a single fiber and having a USP2 size (diameter: 0.59 mm) was mounted to an overflow mould. Next, the suture was pressed and formed at a temperature of 90° C. at a pressure of 140 kgf/cm² for 5 seconds. The thickness of a burr was 50 μm or less. A product was completely separated from the burr due to the overflow space without fissure. A primarily-formed product was heated in a vacuum state at a temperature of 90° C. for 24 hours, so that the primarily-formed product was transformed into a secondarily-formed product. In this case, a force of 14N and a rotation of 72°/cm was applied to two ends thereof. The acicular cogs of the secondarily-formed product were located at positions with rotation of 30° in the two directions, so that a helical multi-directional structure was formed. Therefore, the formed product was appropriate for the object of the present invention.

EXPERIMENTAL EXAMPLE

The tensile strengths of commercialized barbed sutures of A, B, and C companies, the tensile strength of the suture manufactured according to the second embodiment of the present invention, and the spun thread of the suture was compared by a method of measuring plastic tensility. The result of comparison is illustrated in FIG. 3.

Figure 3:
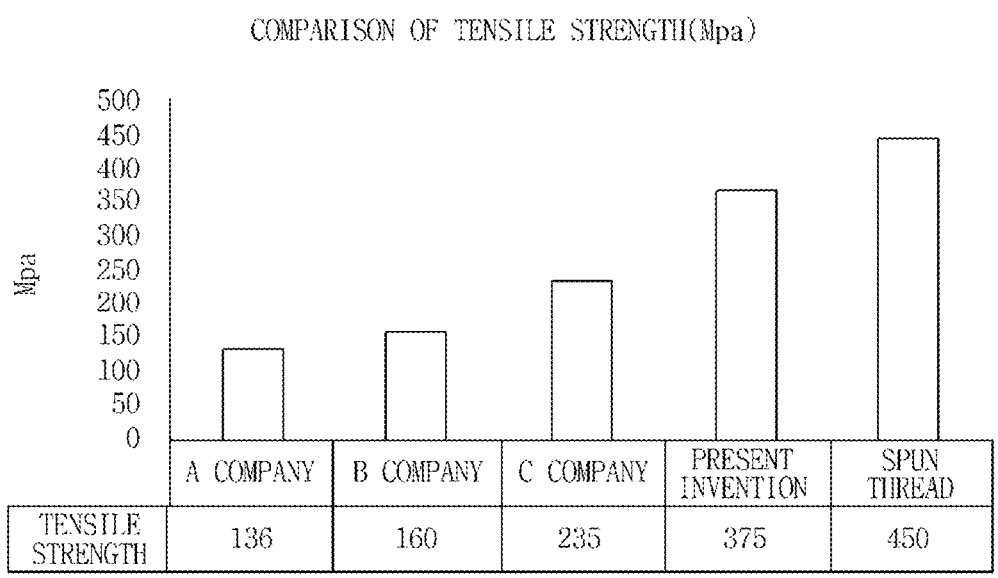
FIG. 3 is a view illustrating a graph of tensile strengths of spun threads of suture produced by a cutting method (A, B, and C companies) and a tensile strength of a spun thread of a suture produced by a method according to the present invention.

As illustrated in FIG. 3, the suture manufactured according to the second embodiment has strength of about 83% of the strength of the spun thread of the suture. It can be understood that the strength of the suture according to the second embodiment is much larger than the strength of the commercialized barbed sutures.

According to the present invention, it is possible to provide a medical suture having functions of allowing micro cogs protruding from a surface thereof to anchor soft tissue in the direction opposite to an insertion direction during the insertion of the medical suture into the soft tissue and generating physical stimulus according to the movement of the medical suture to facilitate regeneration of the tissue and capable of adjusting the size and shape of micro cogs to be used for medical administration such as facelift and wrinkle treatment.

As described hereinbefore, the present invention is not limited to the aforementioned embodiments and the attached drawings. It can be understood by the skilled persons in the related art that various substitutions, modifications, and alterations can be made within the scope of the invention without departing from the spirit of the invention.

COMPARISON OF TENSILE STRENGTH

Tensile Strength
A COMPANY
B COMPANY
C COMPANY
PRESENT INVENTION
SPUN THREAD

What is claimed is:

1. A method of manufacturing a medical suture comprising:
    (1) producing a suture preform where micro cogs are formed on a surface thereof by heating and pressing a raw material of a suture for surgery in an overflow mould at a temperature condition from a point less than a melting point of the raw material of the suture to a point more than a glass transition temperature at a pressure condition from 10 kgf/cm² to 200 kgf/cm² in a heat-press solid-phase forming method; and
    (2) producing a suture with twist maintained by heating the suture preform and applying a tensile force and a rotational force to the suture preform in a vacuum state where the temperature condition from a point less than the melting point of the raw material of the suture to a point more than the glass transition temperature is maintained.

2. Method according to claim 1, wherein the raw material of the suture is a medical polymer material having bio-absorbable property which is made of any one selected among polydioxanone, poly-(1-lactic) acid, poly-glycolic acid, and copolymers thereof.

3. Method according to claim 1, wherein the raw material of the suture is a medical polymer material having non-bio-absorbable property which is made of any one selected among polyprophylene, nylon, and mixtures thereof.

4. Method according to claim 1, wherein the overflow mould is configured so that a gap between a formation space and an overflow space is in a range from 30 μm to 60 μm, an introduction portion of the overflow space has an angle of from 45° to 90°, a depth of the overflow space is in a range from 50 μm to 100 μm, and a width of the overflow space is in a range from 250 μm to 500 μm.

5. Method according to claim 1,
    wherein the tensile force is in a level of from 10% to 30% of a tensile strength of the suture preform, and
    wherein the rotational force corresponds to rotation per unit length of the suture in a range from 72°/cm to 360°/cm.

6. Method according to claim 1, wherein in the step (2), a heating time is in a range from 24 hours to 48 hours.

7. Method according to claim 1,
    wherein a size of the suture is in a range from 0.2 mm to 1 mm in diameter, and
    wherein a height and width of the micro cog are not larger than a diameter of the suture.

8. A medical suture manufactured according to the method according to claim 1,
    wherein the micro cogs are formed on the surface of the suture, wherein rotation per unit length of the suture is applied in a range from 72°/cm to 360°/cm, and wherein the micro cog has a directivity and has an anchoring ability by which the soft tissue is anchored in a direction opposite to an insertion direction when the suture is inserted to the soft tissue.

9. A medical suture manufactured according to the method according to claim 2, wherein the micro cogs are formed on the surface of the suture, wherein rotation per unit length of the suture is applied in a range from 72°/cm to 360°/cm, and wherein the micro cog has a directivity and has an anchoring ability by which the soft tissue is anchored in a direction opposite to an insertion direction when the suture is inserted to the soft tissue.

10. A medical suture manufactured according to the method according to claim 3, wherein the micro cogs are formed on the surface of the suture, wherein rotation per unit length of the suture is applied in a range from 72°/cm to 360°/cm, and wherein the micro cog has a directivity and has an anchoring ability by which the soft tissue is anchored in a direction opposite to an insertion direction when the suture is inserted to the soft tissue.

11. A medical suture manufactured according to the method according to claim 4, wherein the micro cogs are formed on the surface of the suture, wherein rotation per unit length of the suture is applied in a range from 72°/cm to 360°/cm, and wherein the micro cog has a directivity and has an anchoring ability by which the soft tissue is anchored in a direction opposite to an insertion direction when the suture is inserted to the soft tissue.

12. A medical suture manufactured according to the method according to claim 5, wherein the micro cogs are formed on the surface of the suture, wherein rotation per unit length of the suture is applied in a range from 72°/cm to 360°/cm, and wherein the micro cog has a directivity and has an anchoring ability by which the soft tissue is anchored in a direction opposite to an insertion direction when the suture is inserted to the soft tissue.

13. A medical suture manufactured according to the method according to claim 6, wherein the micro cogs are formed on the surface of the suture, wherein rotation per unit length of the suture is applied in a range from 72°/cm to 360°/cm, and wherein the micro cog has a directivity and has an anchoring ability by which the soft tissue is anchored in a direction opposite to an insertion direction when the suture is inserted to the soft tissue.

14. A medical suture manufactured according to the method according to claim 7, wherein the micro cogs are formed on the surface of the suture, wherein rotation per unit length of the suture is applied in a range from 72°/cm to 360°/cm, and wherein the micro cog has a directivity and has an anchoring ability by which the soft tissue is anchored in a direction opposite to an insertion direction when the suture is inserted to the soft tissue.

\* \* \* \* \*